US006756048B1

(12) United States Patent
Sano et al.

(10) Patent No.: US 6,756,048 B1
(45) Date of Patent: Jun. 29, 2004

(54) LONG TIME DRUG-SUSTAINED RELEASE PREPARATION

(75) Inventors: Akihiko Sano, Toyonaka (JP); Hiroo Maeda, Sakai (JP); Masako Kajihara, Itami (JP); Shunsuke Tani, Sakai (JP); Toshihiko Sugie, Toyonaka (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/786,746

(22) PCT Filed: Sep. 6, 1999

(86) PCT No.: PCT/JP99/04809

§ 371 (c)(1),
(2), (4) Date: Apr. 18, 2001

(87) PCT Pub. No.: WO00/15199

PCT Pub. Date: Mar. 23, 2000

(30) Foreign Application Priority Data

Sep. 10, 1998 (JP) ............................................ 10-256170

(51) Int. Cl.⁷ .................................................. A61F 2/00
(52) U.S. Cl. ........................ 424/426; 424/423; 424/424
(58) Field of Search ................................ 424/426, 423, 424/424

(56) References Cited

U.S. PATENT DOCUMENTS

| | | | |
|---|---|---|---|
| 3,279,996 A | | 10/1966 | Long et al. |
| 4,191,741 A | | 3/1980 | Hudson et al. |
| 4,331,651 A | | 5/1982 | Reul et al. |
| 4,985,253 A | * | 1/1991 | Fujioka et al. ............. 424/488 |
| 5,011,692 A | | 4/1991 | Fujioka et al. |
| 5,851,547 A | * | 12/1998 | Fujioka et al. ............. 424/426 |

FOREIGN PATENT DOCUMENTS

| | | | |
|---|---|---|---|
| JP | | 57093909 A | * 6/1982 |
| JP | | A63239212 | 10/1988 |
| JP | | 7330581 | * 12/1995 |

OTHER PUBLICATIONS

Remington's Phamraceutical Science, Eighteenth Edition, 1990, pp. 1307–1308.*
Kim, Sung Ho et al., "Controlled Release of Progesterone from Polyethylene Oxide–Silicone Rubber Matrix", Arch. Pharm. Res. 12(3), pp. 191–194, (1989).
Ozdemir, Nurten et al., "Drug Release from Silicone Matrices I: Influence of Formulation and Shape Factors (*)", IL FARMACO, 50 (7,8), pp. 549–554, (1995).
Pfister, William et al., "Modification of Physical Properties and Drug Delivery Rates from Polydimethylsiloxane by Use of Selected Oil and Water Soluble Additives", Proceed.Intern. Symp. Control. Rel. Bioact. Mater., 12, (1985).
Pfister, William et al., "Methods for Altering Release of Progesterone, Testosterone, Propranolol, and Indomethacin from Silicone Matrices: Effect of Co–Solvents and Inert Fillers", Proceed. Intern, Symp. Control. Rel. Bioact. Mater., 14, (1987), Controlled Release Society, Inc.
Rankin, Fran, et al., "Evaluation of the Compatibility and Physical Properties of Silicone Elastomer Containing Hydrophilic and/or Hydrophobic Additives", Drug Development and Industrial Pharmacy, 13(9–11), pp. 1915–1932, (1987).
Robertson, Dale, et al., "Release Rates of Levonorgestrel from SilasticR Capsules, Homogeneous Rods and Covered Rods in Humans", Contraception, May 1983, vol. 27, No. 5.

* cited by examiner

Primary Examiner—Thurman K. Page
Assistant Examiner—Rachel M. Bennett
(74) Attorney, Agent, or Firm—Birch, Stewart, Kolasch & Birch, LLP

(57) ABSTRACT

The present invention relates to a sustained release preparation of a lipophilic drug, comprising a drug dispersion wherein the lipophilic drug and a water-soluble substance are dispersed, in a solid state at the body temperature of an animal or a human being to which the preparation is to be administered, in a water-impermeable and biocompatible material.

18 Claims, 12 Drawing Sheets

US 6,756,048 B1

LONG TIME DRUG-SUSTAINED RELEASE PREPARATION

This application is the national phase under 35 U.S.C. § 371 of PCT International Application No. PCT/JP99/04809 which has an International filing date of Sep. 6, 1999, which designated the United States of America.

FIELD OF THE INVENTION

The present invention relates to a sustained release preparation for the purpose of maintaining sustained efficacy of a medicine for a human being and an animal.

BACKGROUND OF THE INVENTION

Sustained release of a lipophilic drug has been studied by using a hydrophobic polymer substance as a carrier for a preparation. A principle of release of a lipophilic drug from a hydrophobic polymer is based on diffusion. That is, after a preparation is implanted into the living body, a lipophilic drug moves to surrounding tissues by diffusion from the surface of the preparation, and released thereby. The decreased concentration of the lipophilic drug adjacent to the surface of the preparation leads to movement of the lipophilic drug from an area where the concentration of the drug is high to an area where the concentration of the drug is low, in the state that the drugs were dissolved in a hydrophobic polymer. The movement speed is determined by the concentration gradient and the diffusion coefficient of the drug as described by Fick's first law. Accordingly, as a factor which influences the release rate of the lipophilic drug, there are the concentration of the lipophilic drug in the preparation, the dissolution rate of the lipophilic drug in a carrier, and the diffusion coefficient which is determined by a combination of the lipophilic drug and a carrier.

As a method of controlling the release of a lipophilic drug according to the principle as described above, there are mainly two methods as follows: one of which is a method of coating a layer which contains the lipophilic drug by using a polymer film (capsule method), and another is a method of dispersing the lipophilic drug in a polymer layer (matrix method).

An example of capsule includes Norplant™ (described in U.S. Pat. No. 3,279,996). Norplant™ is a preparation wherein a powdery levonorgestrel is filled in a cylindrical silicone container, of which efficacy can be maintained in the living body during 5 years. A capsule is designed so that the diffusion of a lipophilic drug in a polymer becomes a time-limiting factor. Accordingly, over a period when the concentration of the lipophilic drug in a capsule is higher than the solubility of the lipophilic drug to a polymer film, the drug-release is kept at a constant rate. However, as described in Contraception, 27(5),483–495,1983, the release rate of the drugs is not constant and gradually decline with time. Since the article discloses that the body fluid infiltrates into a capsule in a period during which the preparation has been implanted, it is considered that the concentration of a lipophilic drug in a capsule declined with time, and it led to failure in keeping the release rate of the drug constant. Another example of a capsule is that wherein 50%(w/w) levonorgestrel in a silicone without a filler is filled into a silicone container. A filler is micro particles such as silica (anhydrous silicic acid) which are added to silicone for enhancing the physical strength thereof, of which content is known to influence the release rate of a lipophilic drug. While the preparation shows an almost zero-order release behavior, such zero-order release can be accomplished only when the following conditions are satisfied as described in the above article. Namely, it is necessary that the dissolution and diffusion of a lipophilic drug in a carrier are very rapid and that the rate of the drug diffusing in the wall of a container becomes a rate-limiting factor, thereby the concentration of a lipophilic drug on the surface of the preparation is always kept constant. Because the rates of the lipophilic drug dissolving and diffusing in carrier and container materials depend on the physical features of the lipophilic drug, the carrier and the container materials, a combination of the materials suitable for each of lipophilic drugs must have been determined.

An example of a matrix includes Compudose™ wherein estradiol disperses in silicone (Japanese Patent Publication (Tokkaisho) No. 45694/1980). In the case of the matrix, a lipophilic drug is released from the surface of the preparation, and the concentration of the lipophilic drug around the surface decreases, which leads to diffusion of the lipophilic drug from the central part of the preparation with high concentration of the drug thereby the release of the drug continues. The concentration of the lipophilic drug in a carrier polymer decreases with time, and therefore, the drug usually shows the first-order release behavior that the release rate of the drug decreases with time (Contraception, 27(5), 483–495,1983).

In addition to the purpose of accomplishing the release of the lipophilic drug at a constant rate, several studies have been performed for the purpose of enhancing the release rate of the lipophilic drug from a hydrophobic polymer material. For example, controlling the release rate of a lipophilic drug has been studied by using a liquid additive which has a compatibility with a hydrophobic polymer material such as polyethylene glycol, glycerol and the (Drug Development and Industrial Pharmacy, 13(9–11),1915–1932(1987), Proceed. Intern. Symp. Control. Rel. Bioact. Mater., 14, 223–224(1987), and Arch. Pharm. Res. 12(3), 191–195 (1989)). This aims at enhancing the drug-release by mixing a lipophilic drug with a homogeneous mixture of a hydrophobic polymer material and an additive to improve diffusion of the lipophilic drug in the hydrophobic polymer. In addition, a method using a solid additive such as sodium chloride was also studied (IL PHARMACO, 50(7,8), 549–554(1995)), by which a marked enhancement effect of the drug-release was not obtained. In Proceed Intern. Symp. Control. Rel. Bioact. Mater., 12, 145–146(1985), the rate of a lipophilic drug permeating a film which was prepared by mixing a solid additive such as lactose and sorbitol with silicone was tested, which showed that addition of these substances led to decrease in the permeation rate of the lipophilic drug. In addition, Japanese Patent Publication (Tokkaisho) No. 100315/1980 discloses a silicone rubber-based depot formulation for sustained release of an active component which is characterized by containing a release-enhancing substance dissolved in an amount corresponding to 2–50% by weight of silicone rubber, and specifically the release-enhancing substance includes alcohols, esters, ethers, and ketones which are lipophilic but practically water-insoluble. In all of the method stated above, although the release rate of the lipophilic drug may be enhanced, the typical first-order release behavior is found wherein the drug-release progresses from the entire surface of the preparation and wherein diffusion of lipophilic drug in a carrier is a rate-limiting factor. Thus, the method failed to accomplish a drug-release at a constant rate.

On the other hand, Japanese Patent Publication (Tokkaihei) No. 187994/1995 discloses a technique which allows a sustained release of water-soluble drugs at a constant rate. However, as described in said specification, the mechanism of the release of a lipophilic drug and a water-soluble drug quite differs each other, and therefore, such technique for controlling the release of a water-soluble drug cannot be applied to a lipophilic drug.

As stated above, there is no technique which allows sustained release of a lipophilic drug at a constant rate and which is applicable to various lipophilic drugs until now.

PROBLEM TO BE SOLUBLED BY THE INVENTION

It is generally considered that drug-release in the sustained-release preparation of lipophilic drugs depends on the elution of the drug from the surface of the preparation, at which the drug contacts water, thereby the concentration of the drug in the inside of the preparation decreases, and on the accompanying diffusion of the drug in the preparation. A lipophilic drug is hard to dissolve in water, which suppresses the drug-release from the preparation. Accordingly, in some drugs, the release of a sufficiently effective amount of the drug may not be accomplished. In addition, the drug-release rate depends on the concentration of the drug in the preparation, the amount of the drug which is released during a certain period of time decreases with the decreased concentration of the drug in the preparation. Accordingly, even if the initial drug-release is enough, the released amount of the drug gradually decreases, thereby the constant drug-release cannot be retained. If an additive is added to the preparation to enhance the drug-release, the initial release amount of the drug increases but the drug-release gradually decreases. That is, the constant drug-release over a long period of time cannot be accomplished. In such a situation, it is desired that a sustained release preparation of a lipophilic drug wherein the drug-release can be controlled, and more preferably, one wherein an excess of the initial drug-release is suppressed and wherein the sustained release of the constant amount of drug can be effected over a long period of time.

MEANS TO SOLVE THE PROBLEM

The inventors have eagerly studied for solving the problem and accomplished, as a sustained release preparation of a medicament for a human being and an animal, a sustained release preparation of lipophilic drugs wherein the release of lipophilic drugs, which is usually suppressed because it is hard to dissolve in water, is enhanced, and wherein the release rate thereof can be controlled. By further modifying this preparation, the inventors have accomplished a sustained release preparation of lipophilic drugs which allows suppressing an excessive initial drug-release and effecting sustained release of the practically constant amount of the drug over a long period of time.

That is, the present invention relates to the followings:
[1] A sustained release preparation of a lipophilic drug, comprising a drug dispersion wherein the lipophilic drug and a water-soluble substance are dispersed, in a solid state at the body temperature of an animal or a human being to which the preparation is to be administered, in a water-impermeable and biocompatible material.
[2] The sustained release preparation of a lipophilic drug as described in item [1], which is a rod preparation comprising a drug dispersion and a coating layer, wherein
in said drug dispersion the lipophilic drug and the water-soluble substance are dispersed, in a solid state at the body temperature of an animal or a human being to which the preparation is to be administered, in a water-impermeable and biocompatible material,
said coating layer comprises a water-impermeable and biocompatible material which is same as or different from that used for said drug dispersion, and
said drug dispersion is exposed from the surface of the preparation at one or both end(s) of the axial direction thereof.
[3] The sustained release preparation of a lipophilic drug as described in item [1] or [2] wherein the water-impermeable and biocompatible material is a biocompatible polymer material.
[4] The sustained release preparation of a lipophilic drug as described in item [1] or [2] wherein the water-impermeable and biocompatible material is silicone.
[5] The sustained release preparation of a lipophilic drug as described in any one of items [1]–[4] wherein the water-soluble substance is an amphipathic substance.
[6] The sustained release preparation of a lipophilic drug as described in any one of items [1]–[4] wherein the water-soluble substance is polyethylene glycol, polyoxyethylene polyoxypropylene glycol, or sucrose esters of fatty acids.
[7] The sustained release preparation of a lipophilic drug as described in any one of items [1]–[4] wherein the water-soluble substance is sodium lauryl sulfate or sodium desoxycholic acid.
[8] The sustained release preparation of a lipophilic drug as described in any one of items [1]–[4] wherein the water-soluble substance is sugars.
[9] The sustained release preparation of a lipophilic drug as described in any one of items [1]–[4] wherein the water-soluble substance is an amino acid.
[10] The sustained release preparation of a lipophilic drug as described in any one of items [1]–[4] wherein the water-soluble substance is a water-soluble drug.
[11] The sustained release preparation of a lipophilic drug as described in any one of items [1]–[10] wherein the lipophilic drug is ivermectin, ceftiofur, dexamethasone, or estradiol.

The constitution of the present invention provides the following effects:
(1) The constitution of a drug dispersion that a lipophilic drug and a water-soluble substance are dispersed in a solid state in a water-impermeable and biocompatible material allows consecutively dissolving the water-soluble substances from the surface to the inside of the drug dispersion in water thereby water continuously infiltrates into the inside of the preparation. Thus, a preparation of the present invention controls the extent of the contact of a lipophilic drug water with water in a manner as described above to effect the infiltration of water, thereby the release of the lipophilic drug, which is usually suppressed because the drug is hard to dissolve in water, is enhanced, and its release rate can be controlled.
(2) By selecting a water-soluble substance, the infiltration rate of water in the inside of the preparation can be adjusted, which allows controlling the release rate of lipophilic drugs. In addition, by selecting a water-soluble substance, the dissolution rate of the lipophilic drug can be also controlled due to the dissolution-enhancing effect of a water-soluble substance which is dissolved in water infiltrated into the preparation, on the lipophilic drug. The release rate of a lipophilic substance can be enhanced by using, for example, an amphipathic substance as a water-soluble substance, and the release rate of the lipophilic substance can be varied by adjusting the amount of the water-soluble substance to be used.
(3) In addition, according to the present invention, a cylindrical drug dispersion wherein the lipophilic drug and a water-soluble substance are dispersed in a state of solid in a water-impermeable and biocompatible material is coated with a water-impermeable and biocompatible material to prepare a preparation of the above item [2], thereby the exposed portion of the drug dispersion at the surface of the preparation is limited, which enables controlling the infiltration of water into the inside of said preparation. Thus, by further controlling the extent of contact of the lipophilic drug with water, a preparation of the present invention of the above item [2] suppresses an excessive initial release and a practically constant amount of the drug can be released over a long period of time.

The present invention will be described in detail as follows:

A lipophilic drug and a water-soluble substance may be in any form so long as they are dispersed in the above water-impermeable and biocompatible material in a solid state at the body temperature of an animal or a human being to which the preparation is to be administered, which includes, for example, (1) a homogeneous solid with a lipophilic drug and a water-soluble substance (for example, a solid which is obtained by dissolving the drug and the substance in a solvent in which both of them can be dissolved, followed by removing the:solvent);

(2) a solid wherein the lipophilic drug and the water-soluble substance are in a separate solid, and (3) a solid wherein the lipophilic drug is coated with the water-soluble substance.

To a solid comprising a lipophilic drug and a water-soluble substance, a water-impermeable and biocompatible material, or both of the solid comprising a lipophilic drug and a water-soluble substance, and the water-impermeable and biocompatible material, an additive as mentioned below may be also added A lipophilic drug and a water-soluble substance which are in a solid state at the body temperature of an animal and a human being include those which are in a solid state at a temperature higher at least about 1° C. than the usual body temperature of an animal and a human being. However, when a disease to be treated is accompanied by high fever, they should be in a solid at higher temperature than the usual body temperature.

Specific examples of the temperature higher at least about 1° C. than the usual body temperature of an animal and a human being include usually 38° C. for an preparation to be administered to a human being, 43° C. for an preparation to be used for a disease with high fever, usually 40° C. for an preparation to be administered to an animal (such as, for example, canine, feline, swine, and bovine), and 45° C. for an preparation to be used for a disease with high fever. The body temperature of an animals is described in, for example, Clinical Diagnosis for Veterinary Internal Medicine, 3rd revised & enlarged ed., 2nd ed., R. Nakamura, (Yokendo, 1982), and the minimum temperature at which the lipophilic drug and the water-soluble substance are to be in solid can be determined with reference to such a reference.

A water-impermeable and biocompatible material is acceptable if only it is water-impermeable, biocompatible, and non-disintegrative. In addition, cracking which acts as a pathway of water in a period when a lipophilic drug is releasing may be formed. The term, "non-disintegrative" as herein used, means that it does not quickly disappear by dissolution or degradation when contacted with water, and that the shape at the initial stage can be kept during a desired period.

Preferred a water-impermeable, biocompatible, and non-disintegrative material is a biocompatible polymer material.

As the biocompatible polymer material, there are a non-biodegradable polymer and a biodegradable polymer. Typical examples of the biocompatible polymer material include, but not limited to, for the non-biodegradable polymer, silicone, ethylene-vinyl acetate copolymers, polyethylenes, polypropylenes, polytetrafluoroethylenes, polyurethanes, polyacrylates, polymethacrylates, and so on, preferably silicone, and more preferably Silastic™ Medical Grade ETR Elastomer Q7-4750 or Dow Corning™ MDX-4-4210 Medical Grade Elastomer; and, for the biodegradable polymer, polyesters such as poly-lactic acid-glycolic acid copolymer (PLPG) and poly-lactic acid, poly-amino acids, poly-acid anhydrides. The degradation rate of a biodegradable polymer can vary depending on chemical modification and/or the ratio of the composition, and/or molecular weight thereof, and therefore, a biodegradable polymer having a desired degradation rate can be easily obtained.

A coating layer is for coating a part other than a portion which is selected as a release side for a drug dispersion, and inhibiting infiltration of water into a preparation from a surface thereof other than that where the drug dispersion is exposed. Accordingly, a coating layer material may be biodegradable or non-biodegradable so long as it is water-impermeable, biocompatible, and non-disintegrative during a period when a lipophilic drug is releasing.

Preferred water-impermeable, biocompatible, and non-disintegrative material is a biocompatible polymer material. As a biocompatible polymer material, there are a non-biodegradable polymer and a biodegradable polymer, of which typical examples include, but not limited to, for the non-biodegradable polymer, silicone, ethylene-vinyl acetate copolymers, polyethylenes, polypropylenes, polytetrafluoroethylenes, polyurethanes, polyacrylates, polymethacrylates, and so on, preferably silicone, and more preferably Silastic™ Medical Grade ETR Elastomer Q7-4750 or Dow Corning™ MDX-4-4210 Medical Grade Elastomer; and, for the biodegradable polymer, polyesters such as poly-lactic acid-glycolic acid copolymer (PLPG) and poly-lactic acid, poly-amino acids, poly-acid anhydride. The degradation rate of a biodegradable polymer can vary depending on chemical modification and/or the ratio of the composition, and/or molecular weight thereof, and therefore, a biodegradable polymer having a desired degradation rate can be easily obtained.

A lipophilic drug may be any lipophilic substance so long as it is, as a form of a preparation, in a solid state at the body temperature of an animal or a human being to which the preparation is to be administered. Lipophilic as herein used means that the solubility of a substance to water is low, which specifically includes the following natures, as described in Pharmacopoeia of Japan $13^{th}$ ed. (1996): practically insoluble (the amount of more than or equal to 10000 ml of solvent is required to dissolve 1 g or 1 ml of a solute), very hard to dissolve (the amount of more than or equal to 1000 ml and less than 10000 ml of solvent is required to dissolve 1 g or 1 ml of a solute), or hard to dissolve (the amount of more than or equal to 100 ml and less than 1000 ml of solvent is required to dissolve 1 g or 1 ml of a solute).

Specific example of the a lipophilic drug includes, but not limited to, antibiotics such as avermectin, ivermectin, spiramycin, and ceftiofur; an robials such as amoxicillin, erythromycin, oxytetracycline, and incomycin; anti-inflammatory agents such as dexamethasone and phenylbutasone; hormones such as levothyroxine; adrenocorticosteroids such as dexamethasone palmitate, triamcinolone acetonide, and halopredone acetate; non-steroidal anti-inflammatory agents such as indometacin and aspirin; therapeutic agents for arterial occlusion such as prostaglandin E1; anticancer drugs such as actinomycin and daunomycin; therapeutic agents for diabetes such as acetohexamide; and therapeutic agents for osteopathy such as estradiol. Depending on a disease or a method for application, multiple lipophilic drugs may be contained. In addition to the lipophilic drug having a direct therapeutic effect, the drug may be a substance with a biological activity, and such a substance as promotes or induces a biological activity, which includes an adjuvant for a vaccine, for example saponin. In such a case, incorporation of a vaccine into a preparation results in a sustained release preparation of a vaccine with an adjuvant.

A water-soluble substance is a substance which plays a role of controlling infiltration of water into the inside of the drug dispersion. There is no restriction in term of the water-soluble substance so long as it is in a solid state, as a form of a preparation, at the body temperature of an animal and a human being to which the preparation is to be administered, and a physiologically acceptable, water-soluble substance. In ad dition, only one water-soluble substance, or a combination of two or more water-soluble substances may be used. A water-soluble substance specifically includes synthetic polymers such as polyethylene glycol; sugars such as sucrose, mannitol, glucose, dextran, sodium chondroitin sulfate; amino acids such as glycine and alanine; mineral salts such as sodium chloride; organic salts such as sodium citrate; and proteins such as gelatin and collagen.

It is considered that infiltration of water into the inside of the drug dispersion would occur by infiltrating water into said drug dispersion from a part at which solid particles consisting of a lipophilic drug and a water-soluble substance contact with water (channeling), and infiltrating water into a solution of a lipophilic drug and a water-soluble substance by osmotic pressure to form crack of a water-impermeable and biocompatible material (cracking), through which water infiltrates into the inside of the drug dispersion. Accordingly, the infiltration rate of water would depend on an osmotic pressure of a solution of a lipophilic drug and a water-soluble substance in water.

Generally, the molality of a low molecular weight compound is higher than that of a high molecular weight compound, and therefore, the osmotic pressure for the low molecular weight compound is higher than that for the high molecular weight compound. Accordingly, it is considered that the use of a low molecular weight compound as a water-soluble substance results in an increased effect of an osmotic pressure on the incorporation of water into the drug dispersion, and the incorporation of the larger amount of water accelerates the formation of a pathway of water by cracking of a drug dispersion, thereby infiltration of water into the inside of the drug dispersion is accelerated. As a result, the release-promoting effect on a lipophilic drug can be expected.

In addition, when the water-soluble substance is an amphipathic substance, which dissolves in both an organic solvent and water, it has an effect of controlling the release of a lipophilic drug by altering the solubility thereof. An amphipathic substance includes, but not limited to, polyethylene glycol or a derivative thereof, polyoxyethylene polyoxypropylene glycol or a derivative thereof, fatty acid ester and sodium alkylsulfate of sugars, and more specifically, polyethylene glycol, polyoxyl stearate 40, polyoxyethylene [196]polyoxypropylene[67]glycol, polyoxyethylene[105] polyoxypropylene[5]glycol, polyoxyethylene[160] polyoxypropylene[30]glycol, sucrose esters of fatty acids, sodium lauryl sulfate, sodium oleate, sodium desoxycholic acid: (sodium deoxycholic acid), of which mean molecular weights are more than 1500.

In addition, a water-soluble substance may be a substance which is water-soluble and has any activity in vivo such as low molecular weight drugs, peptides, proteins, glycoproteins, polysaccharides, or an antigenic substance used as vaccines, i.e., water-soluble drugs.

The low molecular weight drugs are exemplified by bleomycin, mitomycin, fluorouracil, peplomycin sulfate, daunorubicine hydrochloride, hydroxyurea, neocarzinostatin, sizofiran, estramustine sodium phosphate, carboplatin, phosphomycin, and so on.

Peptides, proteins, glycoproteins, or polysaccharides are exemplified by cytokines such as interferons and interleukins; hematopoietic factors such as colony-stimulating factors and erythropoietin; hormones such as growth hormone, growth hormone releasing factor, calcitonin, luteinizing hormone, luteinizing hormone releasing hormone, and insulin; growth factors such as somatomedin, nerve growth factor, neurotrophic factors, fibroblast growth factor, and hepatocyte growth factor; cell adhesion factors; immunosuppressants; enzymes such as asparaginase, superoxide dismutase, tissue plasminogen activating factor, urokinase, and prourokinase; proteins involved in bone metabolism such as BMP (Bone Morphogenetic Protein); antibodies; and so on.

For example, a preparation for treating a cancer, wherein the lipophilic drug is actinomycin or daunorubicine, and wherein the water-soluble substance is hematopoietic factors such as G-CSF or GM-CSF, and polyethylene glycol, sucrose, and so on, is expected.

To a solid comprising a lipophilic drug and a water-soluble substance, a water-impermeable and biocompatible material, or both of the solid comprising the lipophilic drug and the water-soluble substance and the water-impermeable and biocompatible material, an additive such as physiologically acceptable stabilizers, solubilizing agents, preservatives, analgesics may be added. A liquid substance may be also added so long as a lipophilic drug and a water-soluble substance in a drug dispersion keep in a solid shape at the body temperature. A surfactant, typical solubilizing agent, can alter an infiltration rate of water and a solubility of a lipophilic drug at the site where water is infiltrated, and therefore, is useful for altering release of the lipophilic drug from the preparation. Specific examples are polysorbate 20, polysorbate 80 and so on.

The release rate of a lipophilic drug from a preparation of the present invention can be controlled for example by the following factors:

(1) Type of a water-soluble substance;
(2) Type of an additive;
(3) Mixing rate of a water-soluble substance and a lipophilic drug;
(4) Total contents of a lipophilic drug, a water-soluble substance, and the other additive in the drug dispersion;
(5) Particle sizes of a lipophilic drug, a water-soluble substance, and the other additive in the drug dispersion; and
(6) Exposed surface area of the drug dispersion.

Total amount of a lipophilic drug, a water-soluble substance, and an additive in a drug dispersion of the present invention is not restricted so long as dispersion and molding are substantially possible, and therefore, will alter depending on the drug dispersion and a coating layer material used. The total content of the lipophilic drug, the water-soluble substance, and the additive in the drug dispersion can be more than 0.1%(W/W) and less than 70%(W/W), preferably more than 1%(W/W) and less than 50%(W/W), and more preferably more than 1%(W/W) and less than 30%(W/W). The content of the lipophilic drug should be variable depending on a type of a lipophilic drug, a disease to be treated, and its severity.

A preparation of the above item [1] may be in any shape so long as it allows the administration in vivo. For example, the preparation may be in rod shape such as cylindrical, prismatic, elliptic cylindrical, or spherical or elliptic spherical shape. The drug dispersion may be composed of one layer or a combination of multiple layers.

The shape of a preparation of the above item [2] may be any rod shapes which specifically include cylindrical, prismatic, and elliptic cylindrical ones. In case of administration via an injection needle, cylindrical shape is preferred Drug dispersion may be in one layer or multiple layers. The cylindrical shape will be more particularly explained below. Thus, in the cross section taken at right angle to the axis of the preparation, it may be two-layer preparation wherein one layer of a drug dispersion is coated by a coating layer, or when having multiple layers of the drug dispersions, it may take the form of concentric circle with a single center of gravity, or may appear as one whose respective centers of gravity lie at different points in the cross section wherein several numbers of drug dispersions are scattered in the cross section. A preparation having multi-layer of drug dispersions may contain the same or a different kind of a lipophilic drug in the respective drug dispersions. As an embodiment of the present invention, a preparation of the above item [2] are shown in FIGS. 1 and 2. That is, FIG. 1 shows oblique views of the outer shape of two-layer preparation, and FIG. 2 shows cross sections of (a) a two-layer preparation, (b) a preparation with a single center of gravity, (c) a preparation with multi-center of gravity.

As a method of preparing a solid comprising a lipophilic drug and a water-soluble substance which is dispersed in a water-impermeable and biocompatible material, a preparation wherein, for example, a homogeneous solid with a lipophilic drug and a water-soluble substance is dispersed in a water-impermeable and biocompatible material can be obtained by dissolving the lipophilic drug and the water-soluble substance in a solvent in which both of them can be dissolved, followed by removing the solvent to give a solid, which is then milled or sieved, if necessary. A solid containing a lipophilic drug, a water-soluble substance, and an additive can be also obtained by adding the additive to the solution obtained above, which is then treated as stated above. As a method of removing a solvent, there is removal by distillation, drying, and so on. Drying may be performed by any method which is conventionally used, which typically includes drying by nitrogen-, helium-, or air-flow, drying in vacuo, air-drying, spray-drying using spray dryer, or a combination thereof.

In the case of a preparation wherein each of a lipophilic drug and a water-soluble substance are dispersed in a water-impermeable and biocompatible material as a separate solid, respective solids of the lipophilic 5 drug and the water-soluble substance can be prepared in the same manner as preparation of a homogeneous solid of a lipophilic drug and a water-soluble substance, followed by mixing the solids. In this procedure, an additive can be also added. In the same manner as preparation of a homogeneous solid of a lipophilic drug and a water-soluble substance, a homogeneous solid of a lipophilic drug and the above additive, or a homogeneous solid of a water-soluble drug and the above additive is prepared, either of which is respectively used as a solid of a lipophilic drug or a water-soluble substance and then mixed with other component(s), or both of which are mixed with other component(s), thereby a solid consisting of a lipophilic drug and a water-soluble substance with an additive can be obtained. When the above mixing is performed, an additive can be further added as well.

The preparation wherein a lipophilic drug is coated with a water-soluble substance can be prepared according to a well-known method such as coacervation method and micro-capsulization by precipitation on the interface of an emulsion (for example, described in "Microcapsule", Kondo et. al., Third Copy, Sankyo Publisher Inc., 1981). At that time, an additive can be added if necessary. The preparation wherein a lipophilic drug is coated with a water-soluble substance can be also prepared by granulation.

A drug dispersion can be prepared by mixing a solid consisting of a lipophilic drug and a water-soluble substance with a water-impermeable and biocompatible material as a carrier component (i.e., to form an apparently homogeneous composition), followed by molding to cure.

Specifically, there are a method wherein a solid comprising a lipophilic drug and a water-soluble substance is mixed with a water-impermeable and biocompatible material in the state of liquid or gel, followed by molding to cure, and a method wherein a solid consisting of a lipophilic drug and a water-soluble substance is added to a solution of a water-impermeable and biocompatible material in a solvent, followed by removing the solvent (for example, by removing by distillation, or drying) to be molded. In case that each of a lipophilic drug and a water-soluble substance are a separate solid particle, they can be added simultaneously or separately. The above additive can be also added if necessary.

In case that a biocompatible material is a biocompatible polymer material, the preparation can be also prepared by the following method. In case that each of a lipophilic drug and a water-soluble substance are a separate solid particle, they can be added simultaneously or separately. The above additive can be also added if necessary.

(1) A method wherein, to a monomer in the state of liquid or gel, a solid consisting of a lipophilic drug and a water-soluble substance is added, mixed, to which a polymerization initiator is added, followed by molding in any shape by filling or extruding, and then curing by polymerization reaction.

(2) A method wherein, to a polymer in the state of liquid or gel, a solid consisting of a lipophilic drug and a water-soluble substance is added, mixed, and then added a cross-linking agent, followed by molding in any shape by filling or extruding, and then curing by cross-linking of polymer. There is also a method wherein cross-linking is initiated by mixing a polymer in the state of liquid or gel containing a cross-linking agent with a polymer in the state of liquid or gel containing a catalyst.

In order to prepare a preparation of the above item [2] of the present invention, a drug dispersion and a coating layer may be prepared separately or simultaneously. For example, a method of preparing a preparation of which shape is a cylinder with a single center of gravity includes, but not limited to, a method wherein a rod-like drug dispersion is prepared, which is coated with a liquid in which a coating layer substance is dissolved, followed by drying, or a method wherein a separately prepared drug dispersion is inserted to the tube which is prepared using a coating layer-constituting substance, a method wherein a drug dispersion is molded in a tube prepared by a substance which constitutes a coating layer, and a method wherein components of a drug dispersion and a coating layer are simultaneously extruded from a nuzzle to be molded. The cylindrical composition wherein the drug dispersion is coated with a coating layer, obtained by the method above, is cut at an appropriate length. Sequentially cutting thereof provides a preparation of which both ends are open.

A preparation of the present invention can be used for various purpose such as treatment or prevention of a disease occurred in an animal such as a human being or pet, or stimulation of growth or birth control. A method for administration includes subcutaneous or intramuscular injection, indwelling in a surgery, intranasal insertion or indwelling, intrarectal insertion or indwelling, for example a suppository, oral administration.

EXAMPLES

Figure 1:
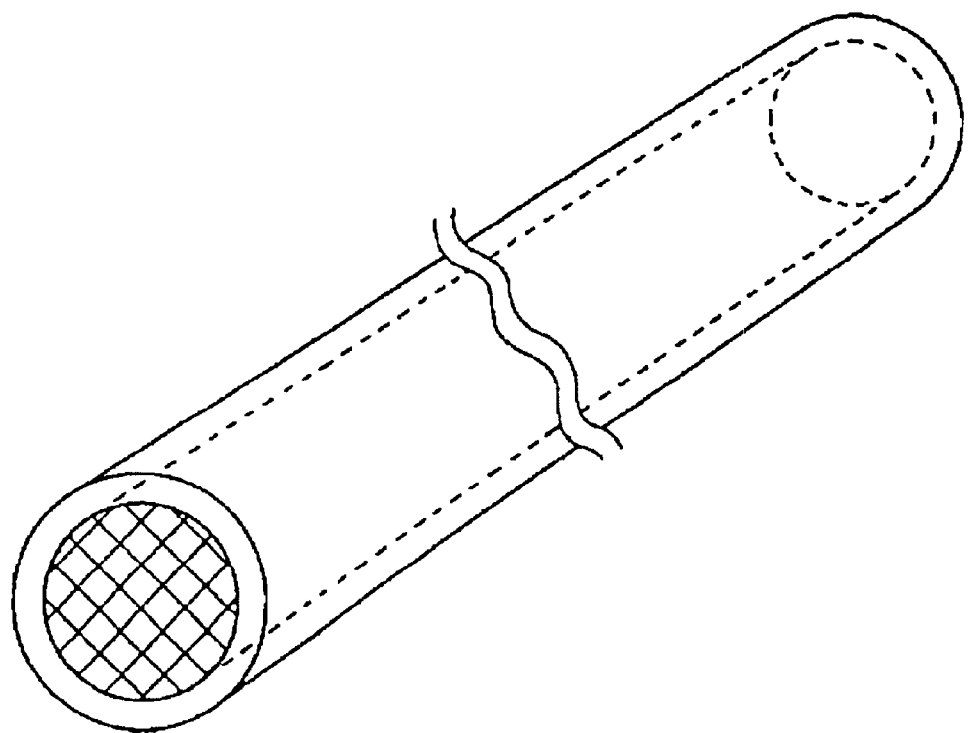
FIG. 1 shows oblique views of a preparation in one embodiment of the present invention.
Figure 2:
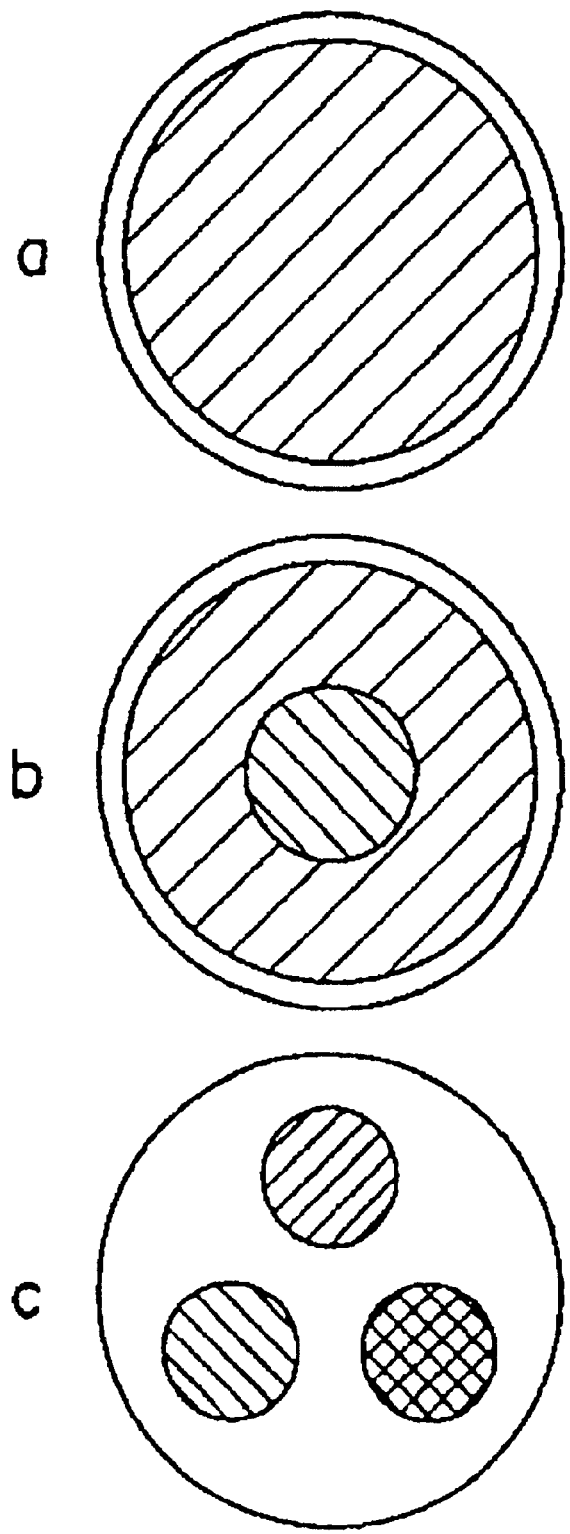
FIG. 2 shows cross sections of a preparation in various embodiments of the present invention.

The present invention will be described in detail by the following Examples and Preparations but the scope of the present invention is not limited thereto.

Example 1

One ml of a solution of 200 mg of ivermectin in methanol and 5 ml of a solution of 1 g of polyethylene glycol 4000 in methanol were mixed, which was dried under nitrogen flow followed by drying in vacuo. The obtained solid was milled, passed through a sieve (212 μm). A portion of a powder thus obtained (450 mg) and Silastic™ Medical Grade ETR Elastomer Q7-4750 Component A (526 mg) and Silastic™ Medical Grade ETR Elastomer Q7-4750 Component B (526 mg) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (1.9 mm of the inner diameter of the outer nozzle, and 1.6 mm of the inner diameter of the inner nozzle) which enables them to be molded by extruding so that the drug dispersion is concentrically coated with the coating layer, and was allowed to stand at room temperature to cure, which was cut to obtain the cylindrical preparation 1 (the length of the preparation is 5 mm, the diameter of the preparation is 2.2 mm, and the diameter of the drug dispersion is 1.7 mm).

Examination 1

Preparation 1 prepared in Example 1 was allowed to stand in a phosphate buffered solution (containing 0.3% polysorbate 20) (1 ml) at 37° C., and then, the quantity of ivermectin released from the preparation was determined by a high performance liquid chromatography to obtain an accumulated release rate thereof. The results are shown in FIG. 3.

Figure 3:
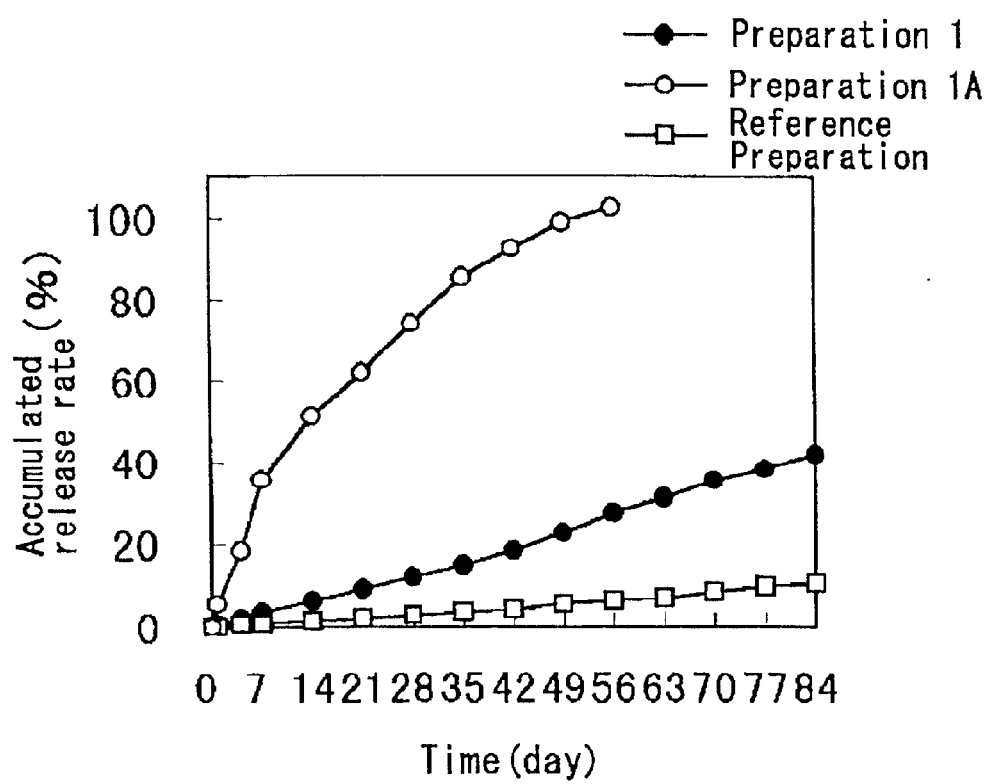
FIG. 3 is a graph showing drug-release behavior of a preparation of the above item [2] (preparation 1), a preparation (preparation 1A) wherein the drug dispersion is not coated with a coating layer, and a preparation (reference preparation) wherein the drug dispersion does not contain a water-soluble substance, in Examination 1 and Examination 3.

As shown in FIG. 3, the release at a constant rate over month-order was achieved in this release examination.

Examination 2

Preparation 1 prepared in Example 1 was subcutaneously administered to a mouse, whole blood was collected from the mouse under anesthesia with ether at the day of determination, and then, the concentration of ivermectin in the plasma was determined by a high performance liquid chromatography. In addition, the preparation which had been administered was removed, eluted with methanol, which was determined by high performance liquid chromatography to obtain the amount of ivermectin remained in the preparation after subcutaneous administration to a mouse. The results thereof are shown in FIG. 4 and FIG. 5.

Figure 4:
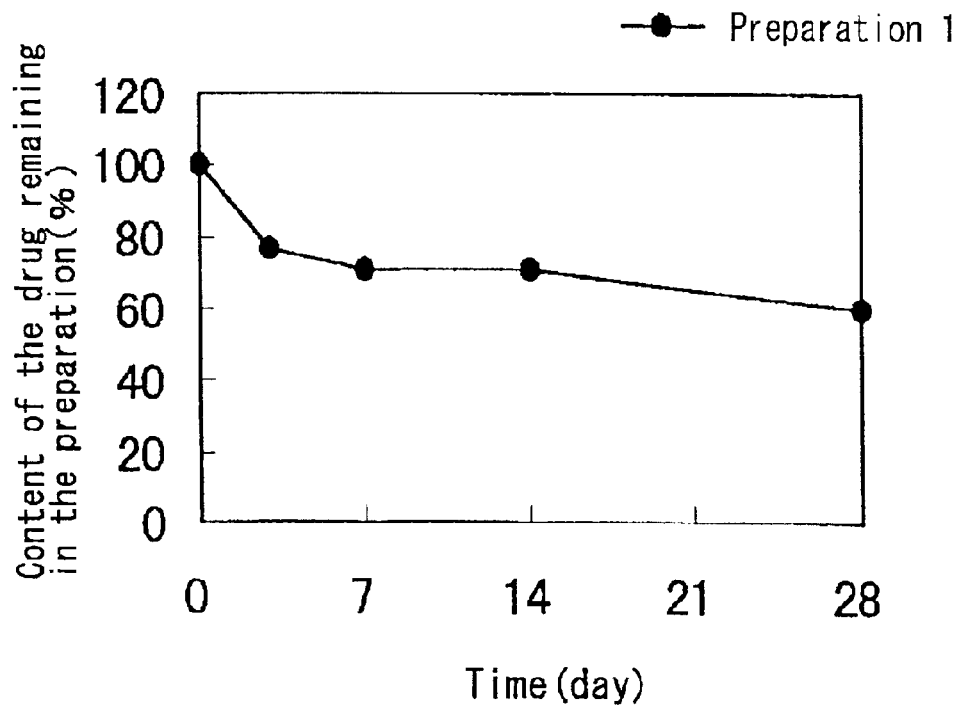
FIG. 4 is a graph showing a time course of the amount of ivermectin remaining in a preparation of the above item [2] (preparation 1) in Examination 2 after it was subcutaneously administered the dorsal region of a mouse (n=3).
Figure 5:
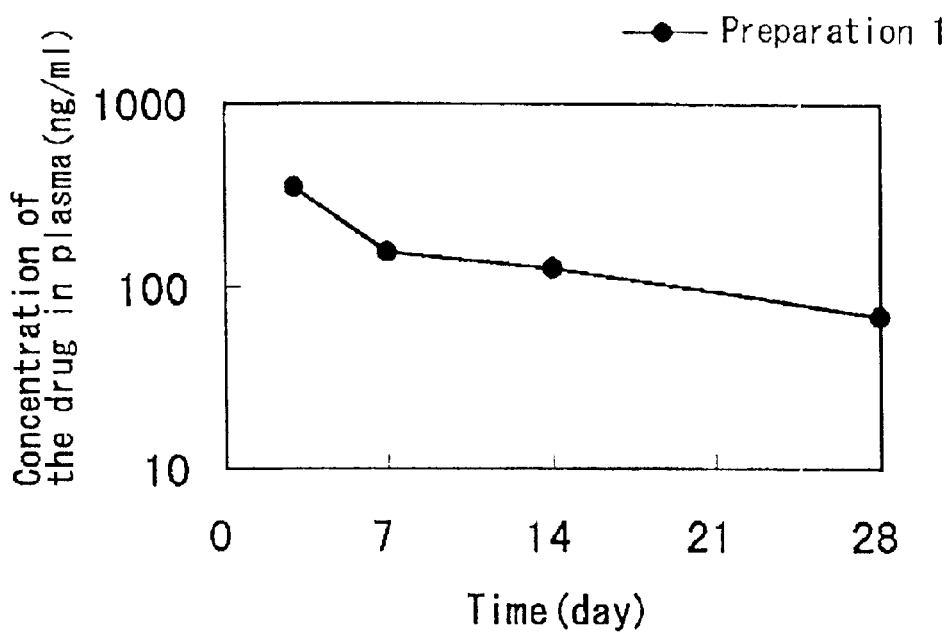
FIG. 5 is a graph showing a time course of the concentration of ivermectin in the plasma in Examination 2 after a preparation of the above item [2] (preparation 1) was subcutaneously administered to the dorsal region of mice (n=3).

As shown in FIG. 4 and FIG. 5, ivermectin remained in the preparation one month after administration, and a high concentration of ivermectin was detected in mouse plasma. This results are considered to show that a lipophilic drug is gradually released at a month-order from a preparation administered to an animal, and then, the concentration of the lipophilic drug in blood can be sustained over the long period of time.

Example 1A

One ml of a solution of 400 mg of ivermectin in methanol and 5 ml of a solution of 2 g of polyethylene glycol 4000 in methanol were mixed, which was dried under nitrogen flow followed by drying in vacuo. The obtained solid was milled, passed through a sieve (212 μm). A portion of a powder thus obtained (300 mg) and Silastic™ Medical Grade ETR Elastomer Q7-4750 Component A (350 mg) and Silastic™ Medical Grade ETR Elastomer Q7-4750 Component B (350 mg) were mixed, which was molded by extruding from a cylindrical nozzle, and then allowed to stand at room temperature to cure, which was cut to obtain the cylindrical preparation 1A (the length of the preparation is 5 mm, the diameter of the preparation is 1.5 mm).

Reference Example 450 mg of powder which was obtained by milling ivermectin followed by passing through a sieve (212 μm), and Silastic™ Medical Grade ETR Elastomer Q7-4750 Component A (526 mg) and Silastic™ Medical Grade ETR Elastomer Q7-4750 Component B (526 mg) were mixed to obtain a drug dispersion component. Silastic™ Medical Grade ETR Elastomer Q7-4750 Component A (50 g) and Silastic™ Medical Grade ETR Elastomer Q7-4750 Component B (50 g) were mixed to obtain a coating layer component. The drug dispersion component and the coating layer component thus obtained were molded by extruding from a double extruder (1.9 mm of the inner diameter of the outer nozzle, and 1.6 mm of the inner diameter of the inner nozzle) which enables them to be molded by extruding so that the drug dispersion is concentrically coated with the coating layer, and was allowed to stand at room temperature to cure, which was cut to obtain the cylindrical reference preparation (the length of the preparation is 5 mm, the diameter of the preparation is 2.2 mm, and the diameter of the drug dispersion is 1.7 mm).

Examination 3

Preparation 1A and reference preparation prepared in Example 1A and Reference Example were tested in the same manner as that for Preparation 1 to obtain an accumulated release rate. The results are shown in FIG. 3.

The release rate of the drug of preparation 1 is faster than that of the reference preparation containing no water-soluble substance, which showed a release-enhancing effect by a water-soluble substance dispersed in a drug dispersion of the preparation of the present invention. In addition, in preparation 1, the drug-release at the initial stage is suppressed and a practically constant release rate is retained over a long period of time in contrast to preparation 1A with no coating layer, which showed the effect of a coating layer.

These results demonstrate that the preparation of the present invention enables the control of the drug-release including the enhancement and suppression of release, and the improvement of a time course of release rate of a lipophilic drug.

Each of preparation 1, preparation 1A and reference preparation were allowed to stand at 37° C. in 1 ml of phosphate buffered solution (containing 0.3% Tween 20) containing a pigment (Blue No. 1), and 2 weeks later, each of the preparations were cut along the axial direction, and observed infiltration of a pigment into the preparations. The results are shown in FIGS. 6–11.

Figure 6:
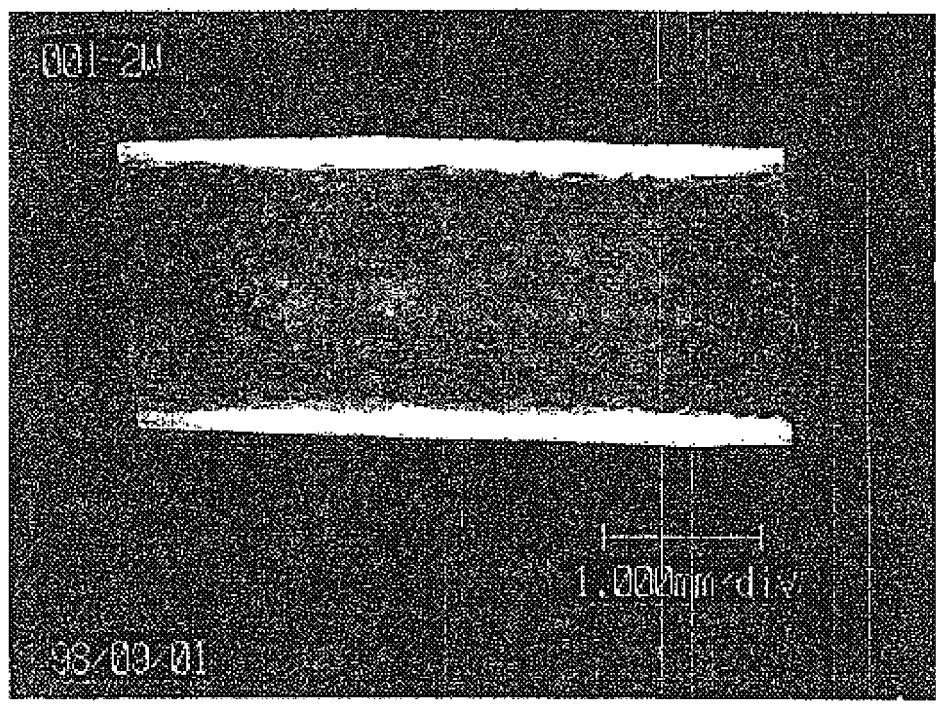
FIG. 6 shows two-valued data by white and black which were obtained by taking in a color photograph of section of a preparation of the above item [2] (preparation 1) by flat-bed scanner using 256-gradation gray scale in Examination 4, followed by dither-processing.
Figure 7:
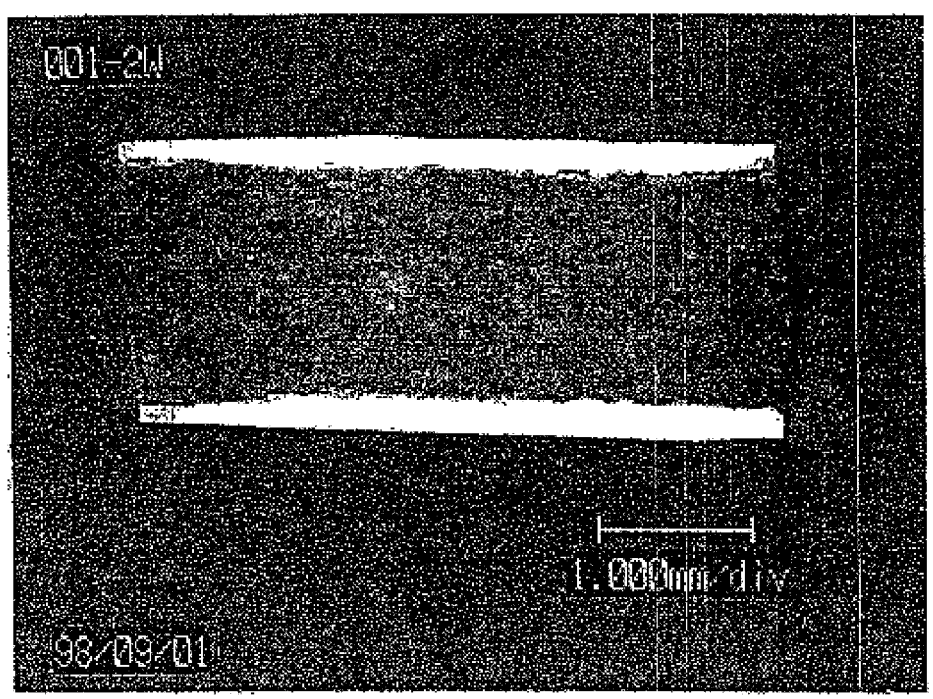
FIG. 7 shows data which were obtained by taking in a color photograph of section of a preparation of the above item [2] (preparation 1) in Examination 4 by flat-bed scanner using 256-color, which was then resolved into RGB data, and red data thus obtained underwent a dither-processing to give two-valued data by white and black thereby blue-colored portion was expressed by black.
Figure 8:
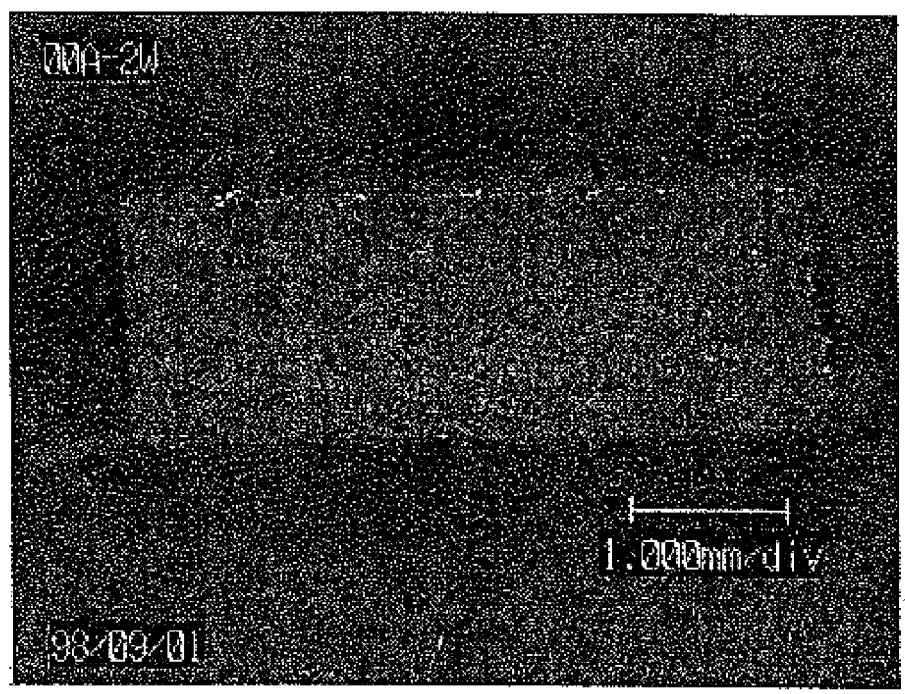
FIG. 8 shows two-valued data by white and black which was obtained by taking in a color photograph of section of a preparation, wherein the drug dispersion of the present invention does not coated with a coating layer, (preparation 1A) in Examination 4 by flat-bed scanner using 256-gradation gray scale, followed by a dither-processing.
Figure 9:
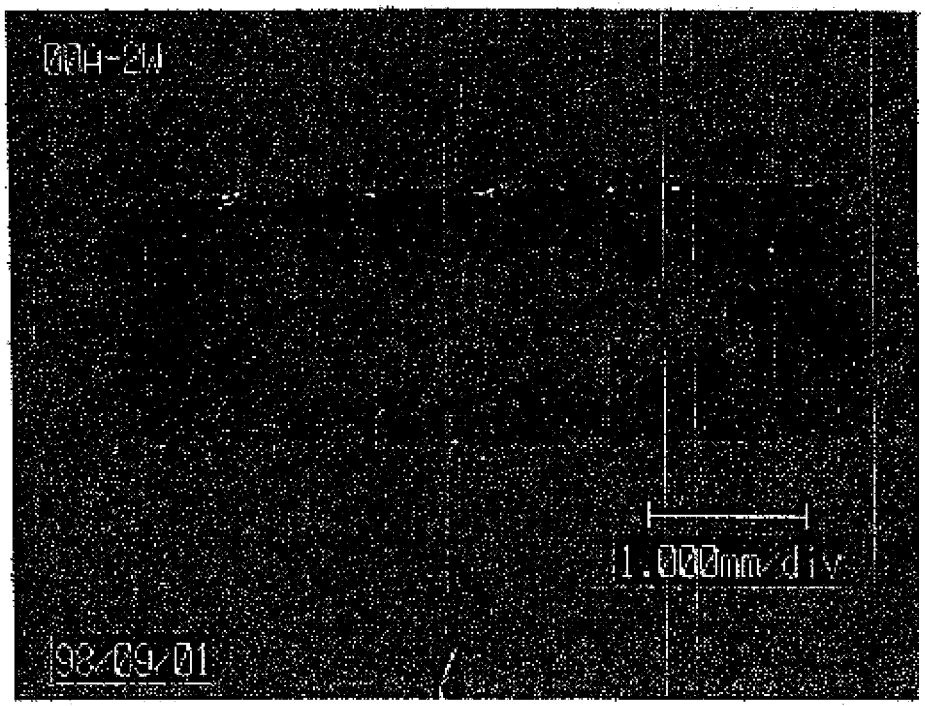
FIG. 9 shows data which were obtained by taking in a color photograph of section of a preparation, wherein the drug dispersion of the present invention does not coated with a coating layer, (preparation 1A) in Examination 4 by flat-bed scanner using 256-color, which was then resolved into RGB data, and red data thus obtained underwent a dither-processing to give two-valued data expressed by white and black thereby blue-colored portion was expressed by black.
Figure 10:
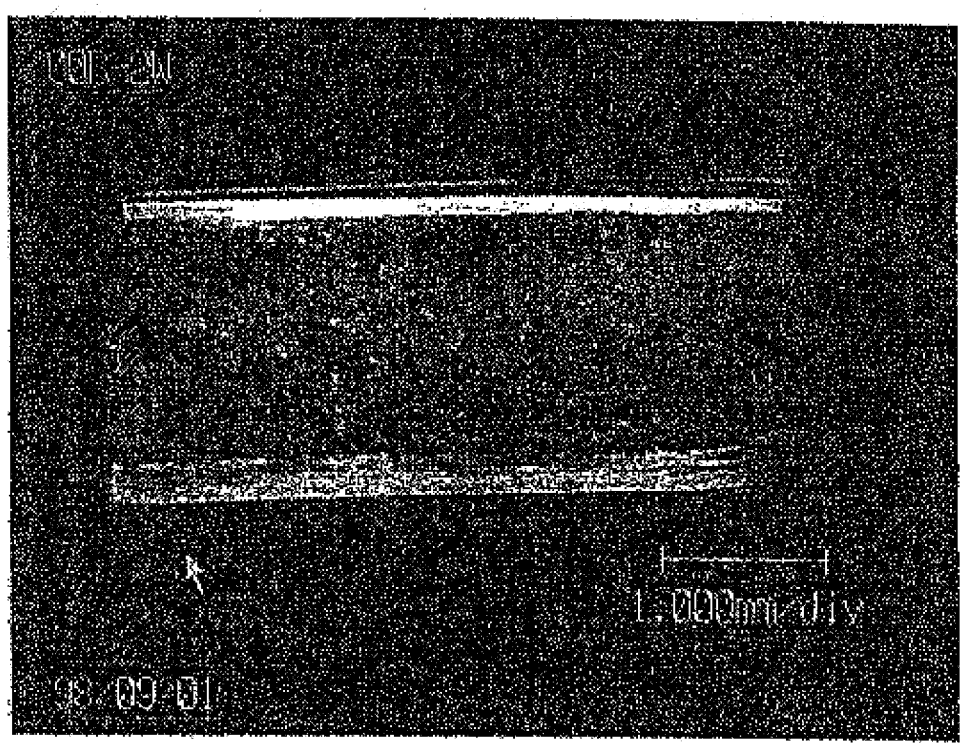
FIG. 10 shows two-valued data by white and black which was obtained by taking in a color photograph of section of a preparation with a coating layer, wherein the drug dispersion does not contained a water-soluble substance, (reference preparation) in Examination 4 by flat-bed scanner using 256-gradation gray scale, followed by a dither-processing.
Figure 11:
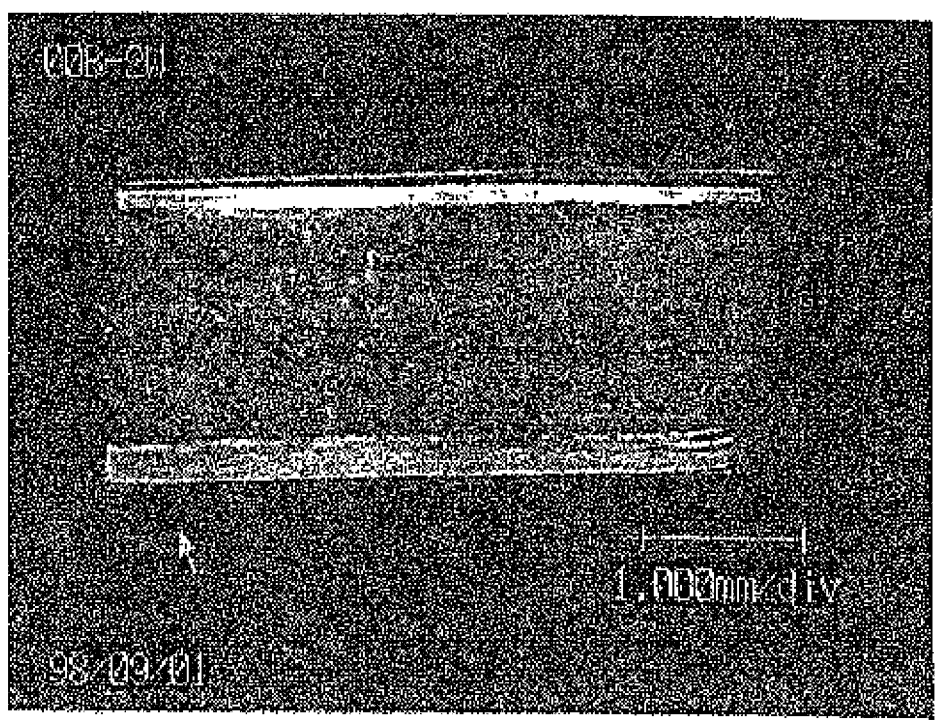
FIG. 11 shows data which were obtained by taking in a color photograph of section of a preparation with a coating layer, wherein the drug dispersion does not contained a water-soluble substance, (reference preparation) in Examination 4 by flat-bed scanner using 256-color, which was then resolved into RGB data, and red data thus obtained underwent a dither-processing to give two-valued data expressed by white and black thereby blue-colored portion was expressed by black.

FIGS. 6, 8 and 10 show two-valued data by white and black which obtained by taking in a color photograph of section of preparations 1 and 1A, and reference preparation by flat-bed scanner using 256-gradation gray followed by dither-processing. FIGS. 7, 9, and 11 show data which was obtained by taking in a color photograph of section of preparations 1 and 1A, and reference preparation by flat-bed scanner using 256-color, which was resolved into RGB data, and red data thus obtained underwent a dither-processing to give two-valued data by white and black thereby blue-colored portion was expressed by black.

In preparation 1A, a pigment infiltrates into the inside of the preparation from the entire surface of the preparation, while infiltration of the pigment in preparation 1 occurs from only the both ends of the drug dispersion which are exposed at the surface of the preparation. The comparison between preparation 1 and preparation 1A demonstrates that infitration of water in preparation 1 is controlled by coating a drug dispersion containing a lipophilic drug with a water-impermeable coating layer.

In preparation 1, infitration of a pigment was observed, while in a reference preparation, only very slight infiltration of a pigment was observed at a part of the preparation. The comparison between preparation 1 and reference preparation demonstrates that infiltration of water in preparation 1 is controlled by a water-soluble substance which is contained in the drug dispersion of the preparation.

Example 2

Preparation 1A was dipped in 10% ethylene-vinyl acetate copolymer (EVA)/chloroform solution, and then, dried at room temperature. Both ends thereof was cut to obtaine preparation 2 (the length of the preparation is 5 mm, the diameter of the preparation is 1.9 mm, the diameter of the drug dispersion is 1.4 mm).

150 mg of powder obtained by milling ivermectin followed by passing through a sieve (212 μm), and 750 mg of powder obtained by milling sucrose followed by passing through a sieve (212 μm) were vigorously shaken, and a portion of the obtained powder mixture (600 mg) and Silastic™ Medical Grade ETR Elastomer Q7-4750 Component A (700 mg) and Silastic™ Medical Grade ETR Elastomer Q7-4750 Component B (700 mg) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (1.9 mm of the inner diameter of the outer nozzle, and 1.6 mm of the inner diameter of the inner nozzle) which enables them to be molded by extruding so that the drug dispersion is concentrically coated with the coating layer which enables them to be molded by extruding so that the drug dispersion is concentrically coated with a coating layer, and was allowed to stand at room temperature to cure, and allowed to stand at room temperature to cure, which was cut to obtain the cylindrical preparation 3 (the length of the preparation is 5 mm, the diameter of the preparation is 2.0 mm, and the diameter of the drug dispersion is 1.6 mm).

The drug dispersion component prepared when preparation 3 was prepared was molded by extruding from a cylindrical nozzle, and further dipped in 10% ethylene-vinyl acetate copolymer (EVA)/chloroform solution, and then, dried at room temperature, followed by cutting to give preparation 4 (the length of the preparation is 5 mm, the diameter of the preparation is 1.9 mm, and the diameter of the drug dispersion is 1.5 mm).

Example 4

Ivermectin (700 mg), polyethylene glycol 4000 (700 mg) and polysorbate 20 (7 mg) were dissolved in methanol (4 ml), dried under nitrogen flow followed by drying in vacuo. The obtained solid was milled and passed through a sieve (212 $\mu$m). A portion (600 mg) of the obtained powder mixture and Silastic™ Medical Grade ETR Elastomer Q7-4750 Component A (700 mg) and Silastic™ Medical Grade ETR Elastomer Q7-4750 Component B (700 mg) were mixed to give a drug dispersion component. Silastic™ Medical Grade ETR Elastomer Q7-4750 Component A (50 mg) and Silastic™ Medical Grade ETR Elastomer Q7-4750 Component B (50 mg) were mixed to give a coating layer component. Thus obtained drug dispersion component and coating layer component were molded by extruding from a double extruder (1.9 mm of the inner diameter of the outer nozzle and 1.6 mm of the inner diameter of the inner nozzle) which enables them to be molded by extruding so that the drug dispersion is concentrically coated with the coating layer which enables them to be molded by extruding so that the drug dispersion is concentrically coated with a coating layer, and was allowed to stand at room temperature to cure, which was cut to obtain the cylindrical preparation 5 (the length of the preparation is 5 mm, the diameter of the preparation is 1.9 mm, and the diameter of the drug dispersion is 1.5 mm).

Example 5

Ivermectin (400 mg) and polyethylene glycol 4000 (2 g) were dissolved in methanol (15ml), to which sodium chloride (400 mg) was added, mixed, and dried under nitrogen flow followed by drying in vacuo. The obtained solid was milled and passed through a sieve(212 $\mu$m). A portion (600 mg) of the obtained powder mixture and Silastic™ Medical Grade ETR Elastomer Q7-4750 Component A (700 mg) and Silastic™ Medical Grade ETR Elastomer Q7-4750 Component B (700 mg) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (1.9 mm of the inner diameter of the outer nozzles and 1.6 mm of the inner diameter of the inner nozzle) which enables them to be molded by extruding so that the drug dispersion is concentrically coated with the coating layer which enables them to be molded by extruding so that the drug dispersion is concentrically coated with a coating layer, and was allowed to stand at room temperature to cure, and was allowed to stand at room temperature to cure, which was cut to obtain the cylindrical preparation 6 (the length of the preparation is 5 mm, the diameter of the preparation is 2.0 mm, and the diameter of the drug dispersion is 1.6 mm).

Example 6

11 ml of a solution of estradiol(300 mg) in methanol and 7.5 ml of a solution of polyethylene glycol 4000 (1.5 g) in methanol were mixed, dried under nitrogen flow followed by drying in vacuo. The obtained solid was milled and passed through a sieve (212 $\mu$m). A portion (300 mg) of the obtained powder mixture and Silastic™ Medical Grade ETR Elastomer Q7-4750 Component A (350 mg) and Silastic™ Medical Grade ETR Elastomer Q7-4750 Component B (350 mg) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (1.9 mm of the inner diameter of the outer nozzles and 1.6 mm of the inner diameter of the inner nozzle) which enables them to be molded by extruding so that the drug dispersion is concentrically coated with the coating layer, and was allowed to stand at room temperature to cure, which was cut to obtain the cylindrical preparation 7 (the length of the preparation is 5 mm, the diameter of the preparation is 2.0 mm, and the diameter of the drug dispersion is 1.7 mm).

Example 7

Ivermectin (28.1 g) and polyethylene glycol 4000 (28.1 mg) were dissolved in methanol (400 ml) by using ultrasonic, which was dried in vacuo by using evaporator and vacuum pump. The obtained solid was milled and passed through a sieve (212 $\mu$m). A portion (2.353 g) of the obtained powder mixture and Silastic™ Medical Grade ETR Elastomer Q7-4750 Component A (2.745 g) and Silastic™ Medical Grade ETR Elastomer Q7-4750 Component B (2.745 g) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (3.0 mm of the inner diameter of the outer nozzle, and 2.7 mm of the inner diameter of the inner nozzle) which enables them to be molded by extruding so that the drug dispersion is concentrically coated with the coating layer, and allowed to stand at 37° C. to cure, which was cut to obtain a cylindrical preparation 8 (the length of the preparation is 7.5 mm, the diameter of the preparation is 2.9 mm, and the diameter of the drug dispersion is 2.3 mm), a cylindrical preparation 9 (the length of the preparation is 30 mm, the diameter of the preparation is 2.9 mm, and the diameter of the drug dispersion is 2.3 mm). a cylindrical preparation 10 (the length of the preparation is 60 mm, the diameter of the preparation is 2.9 mm, and the diameter of the drug dispersion is 2.3 mm).

Example 8

4.35 g of ivermectin passed through a sieve (212 $\mu$m) and 4.35 g of sucrose obtained by milling followed by passing through a sieve (212 µm) were vigorously mixed. A portion of the obtained powder mixture (2.125 g) and Silastic™ Medical Grade ETR Elastomer Q7-4750 Component A (2.479 g) and Silastic™ Medical Grade ETR Elastomer Q7-4750 Component B (2.479 g) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (3.0 mm of the inner diameter of the outer nozzle, and 2.7 mm of the inner diameter of the inner nozzle) which enables them to be molded by extruding so that the drug dispersion is concentrically coated with the coating layer, and allowed to stand at 37° C. to cure, which was cut to obtain the cylindrical preparation 11 (the length of the preparation is 60 mm, the diameter of the preparation is 2.9 mm, and the diameter of the drug dispersion is 2.4 mm).

Example 9

Ivermectin (600 mg) and sodium lauryl sulfate (600 mg) were dissolved in methanol (15 ml), which was dried under nitrogen flow followed by concentrating by using vacuum pump. The obtained solid was milled followed by passing through a sieve (212 µm). A portion of the obtained powder (600 mg) and Silastic™ Medical Grade ETR Elastomer Q7-4750 Component A (700 mg) and Silastic™ Medical Grade ETR Elastomer Q7-4750 Component B (700 mg) were mixed to give a drug dispersion component. Silastic™ Medical Grade ETR Elastomer Q7-4750 Component A (50 g) and Silastic™ Medical Grade ETR Elastomer Q7-4750 Component B (50 g) were mixed to give a coating layer component. Thus obtained drug dispersion component and coating layer component were molded by extruding from a double extruder (1.9 mm of the inner diameter of the outer nozzle, and 1.6 mm of the inner diameter of the inner nozzle) which enables them to be molded by extruding so that the drug dispersion is concentrically coated with a coating layer, and allowed to stand at 37° C. to cure, which was cut to obtain the cylindrical preparation 12 (the length of the preparation is 5 mm, the diameter of the preparation is 1.9 mm, and the diameter of the drug dispersion is 1.5 mm, ivermectin: sodium lauryl sulfate=15:15).

Example 10

Ivermectin (600 mg) and sodium lauryl sulfate (200 mg) were dissolved in methanol (10 ml), which was dried under nitrogen flow followed by concentrating by using vacuum pump. The obtained solid was milled followed by passing through a sieve (212 µm). A portion (400 mg) of the obtained powder and sucrose (200 mg) obtained by milling followed by passing through a sieve (212 µm) were vigorously mixed. According to a method analogous to that of Example 9 and using the powder mixture, a cylindrical preparation 13 was obtained (the length of the preparation is 5 mm, the diameter of the preparation is 2.0 mm, and the diameter of the drug dispersion is 1.5 mm, ivermectin:sodium lauryl sulfate:sucrose=15:15:10).

Example 11

Ivermectin (600 mg) and sodium lauryl sulfate (40 mg) were dissolved in methanol (10 ml), which was dried under nitrogen flow followed by concentrating by using vacuum pump. The obtained solid was milled followed by passing through a sieve (212 µm). A portion (320 mg) of the obtained powder and sucrose (280 mg) obtained by milling followed by passing through a sieve (212 µm) were vigorously mixed. According to the method analogous to that of Example 9 and using the powder mixture (600 mg), a cylindrical preparation 14 was obtained (the length of the preparation is 5 mm, the diameter of the preparation is 1.9 mm, and the diameter of the drug dispersion is 1.5 mm, ivermectin:sodium lauryl sulfate:sucrose=15:1:14).

Example 12

Ivermectin (600 mg) and sodium lauryl sulfate (8 mg) were dissolved in methanol (10 ml), which was dried under nitrogen flow followed by concentrating in vacuo by using vacuum pump. The obtained solid was milled followed by passing through a sieve (212 µm). A portion (304 mg) of the obtained powder and sucrose (296 mg) obtained by milling followed by passing through a sieve (212 µm) were vigorously mixed. According to a method analogous to that of Example 9 and using the powder mixture (600 mg), a cylindrical preparation 15 was obtained (the length of the preparation is 5 mm, the diameter of the preparation is 1.9 mm, and the diameter of the drug dispersion is 1.5 mm, ivermectin:sodium lauryl sulfate:sucrose=15:0.2:14.8).

Example 13

Ivermectin (300 mg) passed through a sieve (212µm) and sucrose (300 mg) obtained by milling followed by passing through a sieve (212 µm) were vigorously mixed. According to the method analogous to that of Example 9 by using the powder mixture (600 mg), a cylindrical preparation 16 was obtained (the length of the preparation is 5 mm, the diameter of the preparation is 2.0 mm, and the diameter of the drug dispersion is 1.4 mm, ivermectin:sucrose=15:15).

Preparation 5

Each of preparations obtained in Example 9–Example 13 (see Table 1) were subcutaneously administered to mice, and at the day of determination, whole blood was collected from the mice under anesthesia with ether. Then, the preparation which had been administered was removed, eluted with methanol, which was determined by high performance liquid chromatography to obtain the content of ivermectin remained in the preparation after subcutaneous administration to mice. The results are shown in FIG. 12.

Figure 12:
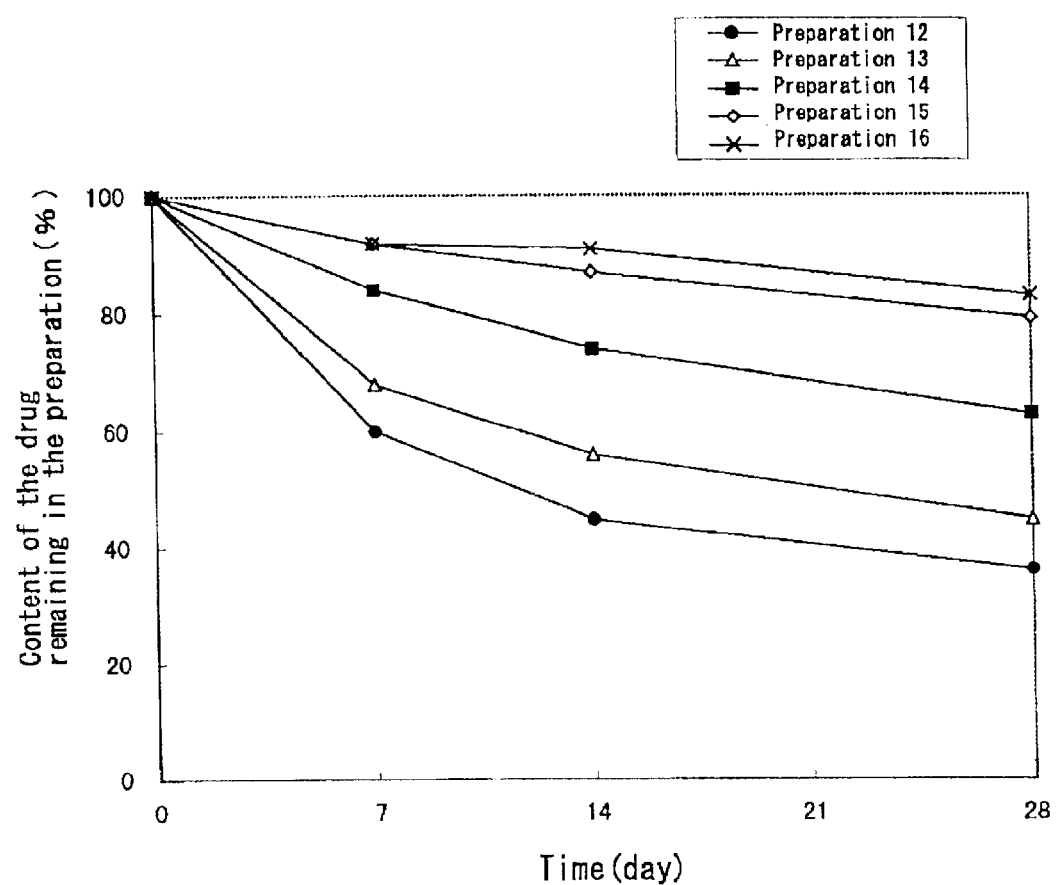
FIG. 12 is a graph showing a time course of the amount of ivermectin remaining in preparations 12–16 (corresponding to a preparation of the above item [2], all of which have a coating layer) in Examination 5 after they were subcutaneously administered to the dorsal region of mice (n=2).

As shown in FIG. 12, by altering the composition of a lipophilic drug and a water-soluble drug which are dispersed in the drug dispersion of the preparation of the present invention, the drug-release rate can be controlled

TABLE 1

| Sample No. | Content (%) of powder in the drug dispersion | Composition of powder ivermectin:sodium lauryl sulfate:sucrose = |
|---|---|---|
| Preparation 12 | 30 | 15:15:0 |
| Preparation 13 | 30 | 15:5:10 |
| Preparation 14 | 30 | 15:1:14 |
| Preparation 15 | 30 | 15:0.2:14.8 |
| Preparation 16 | 30 | 15:0:15 |

Example 14

Ivermectin (600 mg) and sodium desoxycholic acid (600 mg) were dissolved in methanol (15 ml), which was dried under nitrogen flow followed by concentrating in vacuo by using vacuum pump. The obtained solid was milled followed by passing through a sieve (212 μm). A portion (600 mg) of the obtained powder and Silastic™ Medical Grade ETR Elastomer Q7-4750 Component A (700 mg) and Silastic™ Medical Grade ETR Elastomer Q7-4750 Component B (700 mg) were mixed, which was molded by extruding from a cylindrical nozzle, and then allowed to stand at 37° C. to cure, which was cut to obtain a cylindrical preparation 17 (the length of the preparation is 5 mm, the diameter of the preparation is 1.5 mm, ivermectin:sodium desoxycholic acid=15:15).

Example 15

Ivermectin (600 mg) and sodium desoxycholic acid (200 mg) were dissolved in methanol (10 ml), which was dried under nitrogen flow followed by concentrating in vacuo by using vacuum pump. The obtained solid was milled followed by passing through a sieve (212 μm). A portion (400 mg) of the obtained powder and sucrose (200 mg) obtained by milling followed by passing through a sieve (212 μm) were vigorously mixed. According to the method analogous to that of Example 14 and using the powder mixture (600 mg), a cylindrical preparation 18 was obtained (the length of the preparation is 5 mm and the diameter of the preparation is 1.5 mm, ivermectin:sodium desoxycholic acid:sucrose= 15:5:10).

Example 16

Ivermectin (600 mg), sodium desoxycholic acid (200 mg) and polyethylene glycol 4000 (400 mg) were dissolved in methanol (10 ml), which was dried under nitrogen flow followed by concentrating in vacuo by using vacuum pump. The obtained solid was milled followed by passing through a sieve (212 μm). According to a method analogous to that of Example 14 by using a portion (600 mg) of the obtained powder, a cylindrical preparation 19 was obtained (the length of the preparation is 5 mm, the diameter of the preparation is 1.4 mm, ivermectin: sodium desoxycholic acid: polyethylene glycol 4000=15:5:10).

Preparation 6

Figure 13:
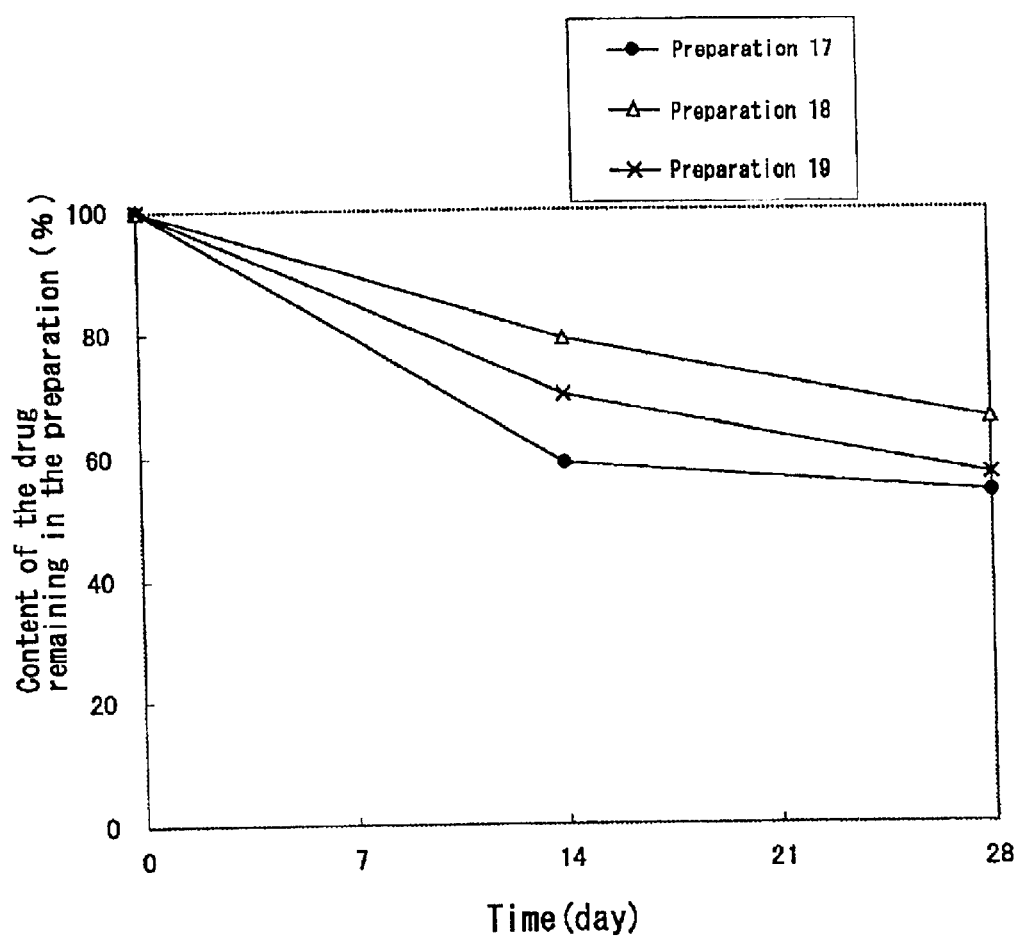
FIG. 13 is a graph showing a time course of the amount of ivermectin remaining in preparations 17–19 (all of which have no coating layer) in Examination 6 after they were subcutaneously administered to the dorsal region of mice (n=2).

Each of preparations obtained in Example 14–Example 16 (see Table 2) were subcutaneously administered to mice, and at the day of determination, whole blood was collected from the mice under anesthesia with ether. Then, the preparation which had been administered was removed, eluted with methanol, which was determined by high performance liquid chromatography to obtain the content of ivermectin remained in the preparation after subcutaneous administration to mice. The results are shown in FIG. 13. As shown in FIG. 13, by altering the composition of a lipophilic drug and a water-soluble drug which are dispersed in the drug dispersion of the preparation of the present invention, the drug-release can be controlled.

TABLE 2

| Sample No. | Content (%) of powder in the drug dispersion | Composition of powder |
| --- | --- | --- |
| preparation 17 | 30 | ivermectin:sodium desoxycholic acid = 15:15 |
| preparation 18 | 30 | ivermectin:sodium desoxycholic acid: sucrose = 15:5:10 |
| preparation 19 | 30 | ivermectin:sodium desoxycholic acid: polyethylene glycol 4000 = 15:5:10 |

EFFECTS OF THE INVENTION

A preparation of the present invention enables the control of drug-release including enhancement and suppression of release of a lipophilic drug, and improvement of variation of the drug-release rate with time. Particularly, a preparation of the above item [2] can persistently release the practically constant amount of a drug over a long period of time.

In addition, controlling the release of a lipophilic drug in a preparation of the present invention can be accomplished by selecting the followings:

(1) Type of a water-soluble substance;

(2) Type of an additive;

(3) Mixture ratio of a water-soluble substance and a lipophilic drug;

(4) Total content of a lipophilic drug, a water-soluble substance and the other additive in a drug dispersion;

(5) Particle size of a lipophilic drug, a water-soluble substance and the other additive in a drug dispersion; and (6) Disposed area of a drug dispersion.

It is claimed:

1. A sustained release preparation of a lipophilic drug, comprising a drug dispersion wherein the lipophilic drug and a water-soluble substance are dispersed, as a solid particle at the body temperature of an animal or a human being to which the preparation is to be administered, in a water-impermeable and biocompatible material, wherein 1 g of the lipophilic drug requires 1000 ml or more of water to be dissolved.

2. The sustained release preparation of a lipophilic drug as claimed in claim 1, which is a rod preparation comprising a drug dispersion and a coating layer, wherein in said drug dispersion the lipophilic drug and the water-soluble substance are dispersed, as a solid particle at the body temperature of an animal or a human being to which the preparation is to be administered, in a water-impermeable and biocompatible material, said coating layer comprises a water-impermeable and biocompatible material which is same as or different from that used for said dispersion, and said drug dispersion is exposed from the surface of the preparation at one or both end(s) of the axial direction thereof.

3. The sustained release preparation of a lipophilic drug as claimed in claim 1 or 2 wherein the water-impermeable and biocompatible material is a biocompatible polymer material.

4. The sustained release preparation of a lipophilic drug as claimed in claim 1 or 2 wherein the water-impermeable and biocompatible material is silicone.

5. The sustained release preparation of a lipophilic drug as claimed in claim 1 or 2 wherein the water-soluble substance is an amphipathic substance.

6. The sustained release preparation of a lipophilic drug as claimed in claim 1 or 2 wherein the water-soluble substance is polyethylene glycol, polyoxyethylene polyoxypropylene glycol, or sucrose esters of fatty acids.

7. The sustained release preparation of a lipophilic drug as claimed in claim 1 or 2 wherein the water-soluble substance is sodium lauryl sulfate or sodium desoxycholic acid.

8. The sustained release preparation of a lipophilic drug as claimed in claim 1 or 2 wherein the water-soluble substance is sugars.

9. The sustained release preparation of a lipophilic drug as claimed in claim 1 or 2 wherein the water-soluble substance is an amino acid.

10. The sustained release preparation of a lipophilic drug as claimed in claim 1 or 2 wherein the water-soluble substance is a water-soluble drug.

11. The sustained release preparation of a lipophilic drug as claimed in claim 1 or 2 wherein the lipophilic drug is ivermectin, ceftiofur, dexamethasone, or estradiol.

12. The sustained release preparation of a lipophilic drug as claimed in claim 4 wherein the water-soluble substance is an amphipathic substance.

13. The sustained release preparation of a lipophilic drug as claimed in claim 4 wherein the water-soluble substance is polyethylene glycol, polyoxyethylene polyoxypropylene glycol, or sucrose esters of fatty acids.

14. The sustained release preparation of a lipophilic drug as claimed in claim 4 wherein the water-soluble substance is sodium lauryl sulfate or sodium desoxycholic acid.

15. The sustained release preparation of a lipophilic drug as claimed in claim 4 wherein the water-soluble substance is sugars.

16. The sustained release preparation of a lipophilic drug as claimed in claim 4 wherein the water-soluble substance is an amino acid.

17. The sustained release preparation of a lipophilic drug as claimed in claim 4 wherein the water-soluble substance is a water-soluble drug.

18. The sustained release preparation of a lipophilic drug as claimed in claim 4 wherein the lipophilic drug is ivermectin, ceftiofur, dexamethasone, or estradiol.

* * * * *